(12) United States Patent
Razavi et al.

(10) Patent No.: US 6,579,822 B2
(45) Date of Patent: Jun. 17, 2003

(54) POLYOLEFIN PRODUCTION

(75) Inventors: Abbas Razavi, Mons (BE); Olivier Miserque, Court-Saint-Etienne (BE)

(73) Assignee: Fina Research, S.A., Feluy (BE)

( * ) Notice: Subject to any disclaimer, the term of this patent is extended or adjusted under 35 U.S.C. 154(b) by 0 days.

(21) Appl. No.: 10/066,440

(22) Filed: Jan. 31, 2002

(65) Prior Publication Data

US 2002/0133034 A1 Sep. 19, 2002

Related U.S. Application Data

(62) Division of application No. 09/459,836, filed on Dec. 13, 1999.

(30) Foreign Application Priority Data

Dec. 14, 1998 (EP) .............................. 98123747

(51) Int. Cl.[7] .................. B01J 31/00; C07F 17/00; C08F 4/44
(52) U.S. Cl. ................. 502/103; 502/117; 502/120; 526/168; 526/351; 526/943; 556/11; 556/12; 556/43; 556/53
(58) Field of Search .................. 556/11, 12, 43, 556/53; 502/103, 117, 120; 526/168, 943, 351

(56) References Cited

U.S. PATENT DOCUMENTS 5,808,122 A  9/1998 Herrmann et al. ............ 556/58

FOREIGN PATENT DOCUMENTS

| EP | 0 420 436 A1 | * 4/1991 |
| EP | 0764653 | 3/1997 |
| WO | 9205204 | 4/1992 |
| WO | 9500562 | 1/1995 |

OTHER PUBLICATIONS

"Application of Amine Elimination for the Efficient Preparation of Electrophillic Ansa–Monocyclopentadienyl Group 4 Complexes Containing an Appended Amido Functionality. Structural Characterization of [(C5H4)SiMe2 (N–t–Bu)] Zrc12(NMe2H)"; Donald W. Carpenetti, et. al., Organomettalics, vol. 15 (II), p. 1573 (1996).

* cited by examiner

Primary Examiner—Porfirio Nazario-Gonzalez
(74) Attorney, Agent, or Firm—Gilbreth & Associates

(57) ABSTRACT

A metallocene compound having the general formula: $CpAXMQ_1Q_2Cp'A'X'M'Q_1'Q_2'$ wherein Cp and Cp' are each independently a substituted or unsubstituted cyclopentadienyl moiety; M and M' are each independently a metal chosen from Group IV B transition metals and vanadium, and coordinate to Cp and Cp' respectively; X and X' are each independently a substituted or unsubstituted Group VA or VIA heteroatom and coordinate to M and M' respectively; A and A' are bridging groups between Cp and X and between Cp' and X' respectively and are independently chosen from $-SiR'_2-O-SiR'_2-$, $-Si_nR'_m-$, $-C_nR'_m-$ and $-CR'_2-SiR'_2-CR'_2-SiR'_2-$, in which each R' is independently H or hydrocarbyl having 1 to 20 carbon atoms, n is an integer in the range 1 to 4 and m=2n; each $Q_1$, $Q_2$ and $Q_1'$ and $Q_2'$ is independently a coordinating group which is hydrogen, halogen or hydrocarbyl having 1 to 20 carbon atoms and each of $Q_1$ and $Q_1'$ is coordinated to both M and M'.

23 Claims, 3 Drawing Sheets

POLYOLEFIN PRODUCTION

The present application is a Divisional Application of and claims benefit under 35 U.S.C. 120 of U.S. patent application Ser. No. 09/459,836, filed Dec. 13, 1999, entitled "Polyolefin Production."

The present invention relates to a metallocene catalyst component for use in preparing isotactic polyolefins, especially polypropylenes. The invention further relates to a catalyst system which incorporates the metallocene catalyst component and a process for preparing such isotactic polyolefins.

Olefins having 3 or more carbon atoms can be polymerised to produce a polymer with an isotactic stereochemical configuration. For example, in the polymerisation of propylene to form polypropylene, the isotactic structure is typically described as having methyl groups attached to the tertiary carbon atoms of successive monomeric units on the same side of a hypothetical plane through the main chain of the polymer. This can be described using the Fischer projection formula as follows:

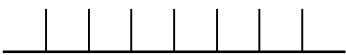

Another way of describing the structure is through the use of NMR spectroscopy. Bovey's NMR nomenclature for an isotactic pentad is . . . mmmm with each "m" representing a "meso" diad or successive methyl groups on the same side in the plane.

In contrast to the isotactic structure, syndiotactic polymers are those in which the methyl groups attached to the tertiary carbon atoms of successive monomeric units in the chain lie on alternate sides of the plane of the polymer. Using the Fischer projection formula, the structure of a syndiotactic polymer is described as follows:

In NMR nomenclature, a syndiotactic pentad is described as . . . rrrr . . . in which "r" represents a "racemic" diad with successive methyl groups on alternate sides of the plane.

In contrast to isotactic and syndiotactic polymers, an atactic polymer exhibits no regular order of repeating unit. Unlike syndiotactic or isotactic polymers, an atactic polymer is not crystalline and forms essentially a waxy product.

WO96/00734 relates to "constrained geometry" complexes which are said to be useful as catalysts in the production of polyethylene. Some of the constrained geometry metallocenes according to WO96/00734 have a bridge between the cyclopentadienyl ring and the metal which includes a divalent heteroatom ligand. These constrained geometry metallocenes are not reported for production of polypropylenes.

In Polymer Preprints 37(2), p474 of 1996, McKnight et al report that some Group IV mono-cyclopentadienyl amido complexes may be used as catalysts in the production of polypropylene but that the polymer product is almost completely atactic.

In contrast, the present applicants have surprisingly found that isotactic polypropylene may be produced using constrained geometry metallocene catalysts, especially from a novel class of dimeric metallocene compounds.

In a first aspect, the present invention provides a metallocene compound having the general formula: $CpAXMQ_1Q_2Cp'A'X'M'Q'_1Q'_2$ wherein Cp and Cp' are each independently a substituted or unsubstituted cyclopentadienyl moiety; M and M' are each independently a metal chosen from Group IV B transition metals and vanadium, and coordinate to Cp and Cp' respectively; X and X' are each independently a substituted or unsubstituted Group VA or VIA heteroatom and coordinate to M and M' respectively; A and A' are bridging groups between Cp and X and between Cp' and X' respectively and are independently chosen from $-SiR'_2-O-SiR'_2-$, $-Si_nR'_m-$, $-C_nR'_m-$ and $-CR'_2-SiR'_2-CR'_2-SiR'_2-$, in which each R' is independently H or hydrocarbyl having 1 to 20 carbon atoms, n is an integer in the range 1 to 4 and m=2n; each $Q_1$, $Q_2$ and $Q_1'$ and $Q_2'$ is independently a coordinating group which is hydrogen, halogen or hydrocarbyl having 1 to 20 carbon atoms and each of Q and $Q_1'$ is coordinated to both M and M'.

Preferably, at least one of Cp and Cp' is substituted.

The metallocene compound preferably has a dimeric structure and preferably also has an active site with local C2 symmetry.

The metallocene may be used as a catalyst component for the production of a polyolefin, especially isotactic polypropylene.

In a further aspect, the present invention provides a catalyst system or use in preparing polyolefins which comprises (as a metallocene compound as defined above; and (b) an aluminium- or boron-containing cocatalyst capable of activating the metallocene compound. Suitable aluminium-containing cocatalysts comprise an alumoxane, an alkyl aluminium and/or a Lewis acid.

The alumoxanes usable in the process of the present invention are well known and preferably comprise oligomeric linear and/or cyclic alkyl alumoxanes represented by the formula:

for oligomeric, linear alumoxanes and

for oligomeric, cyclic alumoxane, wherein n is 1–40, preferably 10–20, m is 3–40, preferably 3–20 and R is a $C_1$–$C_8$ alkyl group and preferably methyl. Generally, in the preparation of alumoxanes from, for example, aluminium trimethyl and water, a mixture of linear and cyclic compounds is obtained.

Suitable boron-containing cocatalysts may comprise a triphenylcarbenium boronate such as tetrakis-pentafluorophenyl-borato-triphenylcarbenium as described in EP-A-0427696, or those of the general formula $[L'-H]^+ [B\ Ar_1\ Ar_2\ X_3\ X_4]^-$ as described in EP-A-0277004 (page 6, line 30 to page 7, line 7).

The catalyst system may be employed in a solution polymerisation process, which is homogeneous, or a slurry process, which is heterogeneous. In a solution process, typical solvents include hydrocarbons with 4 to 7 carbon atoms such as heptane, toluene or cyclohexane. In a slurry process it is necessary to immobilise the catalyst system on an inert support, particularly a porous solid support such as talc, inorganic oxides and resinous support materials such as polyolefin. Preferably, the support material is an inorganic oxide in its finally divided form.

Suitable inorganic oxide materials which are desirably employed in accordance with this invention include Group 2a, 3a, 4a or 4b metal oxides such as silica, alumina and mixtures thereof. Other inorganic oxides that may be employed either alone or in combination with the silica, or alumina are magnesia, titania, zirconia, and the like. Other suitable support materials, however, can be employed, for example, finely divided functionalized polyolefins such as finely divided polyethylene. Preferably, the support is a silica having a surface area comprised between 200 and 900 $m^2/g$ and a pore volume comprised between 0.5 and 4 ml/g.

The amount of alumoxane and metallocenes usefully employed in the preparation of the solid support catalyst can vary over a wide range. Preferably the aluminium to transition metal mole ratio is in the range between 1:1 and 100:1, preferably in the range 5:1 and 50:1.

The order of addition of the metallocenes and alumoxane to the support material can vary. In accordance with a preferred embodiment of the present invention alumoxane dissolved in a suitable inert hydrocarbon solvent is added to the support material slurried in the same or other suitable hydrocarbon liquid and thereafter a mixture of the metallocene catalyst component is added to the slurry.

Preferred solvents include mineral oils and the various hydrocarbons which are liquid at reaction temperature and which do not react with the individual ingredients. Illustrative examples of the useful solvents include the alkanes such as pentane, iso-pentane, hexane, heptane, octane and nonane; cycloalkanes such as cyclopentane and cyclohexane, and aromatics such as benzene, toluene, ethylbenzene and diethylbenzene.

Preferably the support material is slurried in toluene and the metallocene and alumoxane are dissolved in toluene prior to addition to the support material.

Without wishing to be bound by any theory, it is possible that the dimeric metallocene compounds described above may, in use, form corresponding monomeric compounds which act as the active catalytic species. Accordingly, the dimeric compounds may be precursors for active monomeric compounds.

In a further aspect, the present invention provides a process for preparing polyolefins, particularly isotactic polypropylenes, which comprises contacting the catalyst system with at least one olefin in a reaction zone under polymerisation conditions. The olefin is preferably propylene.

In a further aspect, the present invention provides use of a catalyst comprising a metallocene compound for the production of isotactic polypropylene, wherein the metallocene compound has the general formula $CpAXMQ_2$, in which Cp is a cyclopentadienyl moiety substituted so that when in use isotactic polypropylene is produced; M is a metal chosen from Group IV B transition metals and vanadium, and coordinates to Cp; X is a substituted or unsubstituted Group VA or VIA heteroatom which coordinates to M; A is a bridging group between Cp and X which is chosen from $-SiR'_2-O-SiR'_2-$, $-Si_nR'_m-$, $-C_nR'_m-$ $-CR'_2-SiR'_2-CR'_2-SiR'_2-$, in which each R' is independently H or hydrocarbyl having 1 to 20 carbon atoms, n is an integer in the range 1 to 4 and m=2n; and each Q is independently hydrogen, halogen or hydrocarbyl having 1 to 20 carbon atoms. The metallocene compound preferably has an active site with local C1 symmetry when the active catalyst is in the form of a monomer.

Preferably, each cyclopentadienyl moiety is a substituted or unsubstituted indenyl, more preferably a substituted or unsubstituted benzoindenyl. A preferred substitution position is position 2 in the cyclopentadienyl ring, the substituent of which may be hydrocarbyl having 1 to 20 carbon atoms, such as methyl.

M is preferably Zr.

Each heteratom is preferably nitrogen, phosphorus, oxygen or sulphur so as to provide a suitable divalent ligand for constraining the geometry of the metallocene. The heteroatom is typically substituted with H, hydrocarbyl having 1 to 20 carbon atoms or silyl and is preferably nitrogen. Each A and A' is preferably $SiR'_2$ wherein each R' is preferably methyl.

In a further aspect of the invention, there is provided use of a metallocene compound as described above wherein the metallocene compound is formed from a dimeric metallocene compound also as described above.

The invention will now be described in further detail, by way of example only, with reference to the following Examples and accompanying drawings, in which.

EXAMPLE 1

Figure 1:
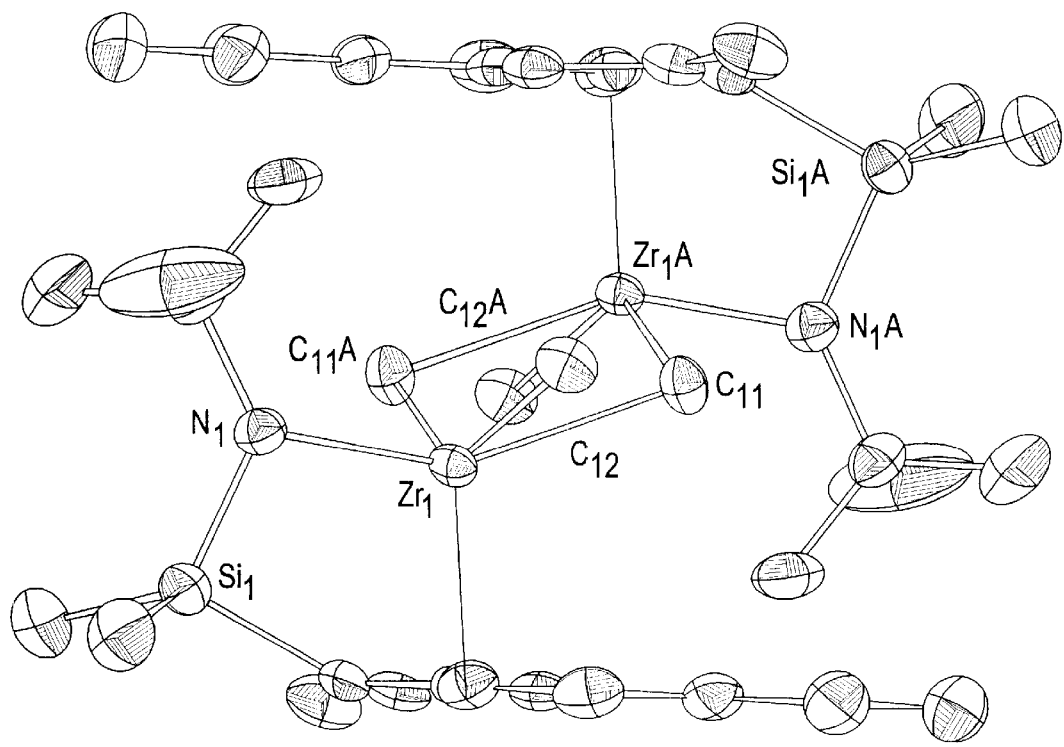
FIG. 1 shows the results of crystal structure analysis for $(Me_2Si(^tbuN)(2-MeBenzInd)ZrCl_2)_2$.

Preparation of the Dimer of (t-Butylamido) (2-methyl-4,5-benzoinden-1-yl)-1,1-dimethylsilane Zirconium Dichloride 1. (2-Methyl-4,5-benzoinden-1-yl,)-1,1-dimethylsilyl-t-butylamine A solution of 83.2 mmol of 2-methyl-4,5-benzoindene in 150 cc of diethylether was added dropwise at room temperature to a solution of 83.0 mmol of dichlorodimethylsilane in 100 cc of diethylether. The mixture was stirred overnight at room temperature and then transferred on a solution of 83.0 mmol of t-butylamidolithium in 300 cc of diethylether. After the mixture has been stirred for 8 hours, the precipitated lithium chloride was eliminated by filtration. The solution was concentrated under vacuum and 250 cc of n-pentane were added to the residue. The brown solid which precipitated after 1 hour at 20° C. was filtered off and dried under an oil-pump vacuum. 20.6 g (80%) of (t-butylamido) (2-methyl-4,5-benzoinden-1-yl)-1,1-dimethylsilane were obtained.

2. Preparation of Dilithio Salt, (2-Methyl-4,5-benzoinden-1-yl)-1,1-dimethylsilyl-t-butylamide:

10.0 g (32.3 mmol) of (t-butylamido) (2-methyl-4,5-benzoinden-1-yl)-1-1-dimethylsilane were dissolved in 200 cc of diethylether and 40.4 cc (64.6 mmol) of 1.6 molar diethylether solution of methyllithium were added dropwise at room temperture. After the mixture has been stirred overnight, the solvent was removed under vacuum. The brown residue was washed several times with n-pentane and dried under vacuum. 11.9 g of the dilithio salt were obtained as a brown powder.

3. Preparation of (2-Methyl-4,5-benzo-inden-1-yl)-1,1-dimethylsilyl-t-butylamido Zirconium Dichloride:

11.9 g of the dilithio salt was suspended in 200 cc of pentane and 7.6 g (32.6 mmol) of zirconium tetrachloride were added in small portions. The mixture was stirred for 10 hours at room temperature. The resulting yellow solid was filtered off, washed several times with n-pentane and dried under vacuum. The solid was suspended in 500 cc of n-hexane and heated under reflux for 1 hour. The yellow solid was then eliminated by filtration at 50° C. and the filtrate concentrated under vacuum. 1.9 g (12a) of (t-butylamido) (2-methyl-4,5-benzoinden-1-yl)-1,1-dimethylsilane zirconium dichloride were obtained as the dimer structure determined by X-ray diffraction analysis (yellow crystals were obtained by recrystallization in dichloromethane). 1H NMR spectrum (300 MHz, CD2C12, d in ppm): 8.09–7.37 (m, 7H, 2-MebenzInd-H), 2.43 (s, 3H, 2—CH3-benzInd), 1.31 (s, 9H, t-BuN), 0.87 and 0.71 (s, 3H, Me2Si).

EXAMPLE 2

Preparation of the Dimer of (t-Butylamido) (2-methyl-4,5-benzoinden-1-yl)-1,1-dimethylsilane Titanium Dichloride The procedure described in Example I was repeated with TiC14 being used instead of ZrCl4. 1H NMR spectrum (300 MHz, CD2C12, d in ppm): 8.08–7.32 (m, 7H, 2-MebenzInd-H), 2.47 (s, 3H, 2—CH3-benzInd), 1.48 (s, 9H, t-BuN), 0.98 and 0.84 (s, 3H, Me2Si)

EXAMPLE 3

Polymerisation Procedures

Each polymerisation was performed in a 4 liter bench reactor wit, pure polypropylene or with diluent such as cyclohexane or isobutane with the quantities reported in the following Tables. Polymerisation was initiated by introducing metallocene (1 to 10 mg) precontacted with 1 ml of MAO (methylaluminoxane) (30% solution in toluene obtained from WITCO) three minutes prior to its introduction into the reactor.

Table 1 shows the results of polypropylene production using the catalyst of Example 1 in an amount of 2.8 mg in 2 l diluent with 850 ppm cocatalyst. A polymer with a high melting point is obtained in the form of a crystalline powder. 13C NMR analysis confirms that the polypropylene is isotactic and Table 2 shows the pentad intensity distribution thereof. A high mmmm pentad intensity of 87% is observed with mm triads of 93% and m dyads of 95.5%. These results are comparable to those obtained with polypropylenes made using highly stereoselective stereorigid classical metallocene based catalysts. The relatively low occurence of 2-1 and 1-3 regiodefects is very surprising. The high stereoregularity of the polymer explains the high melting point observed.

Figure 2:
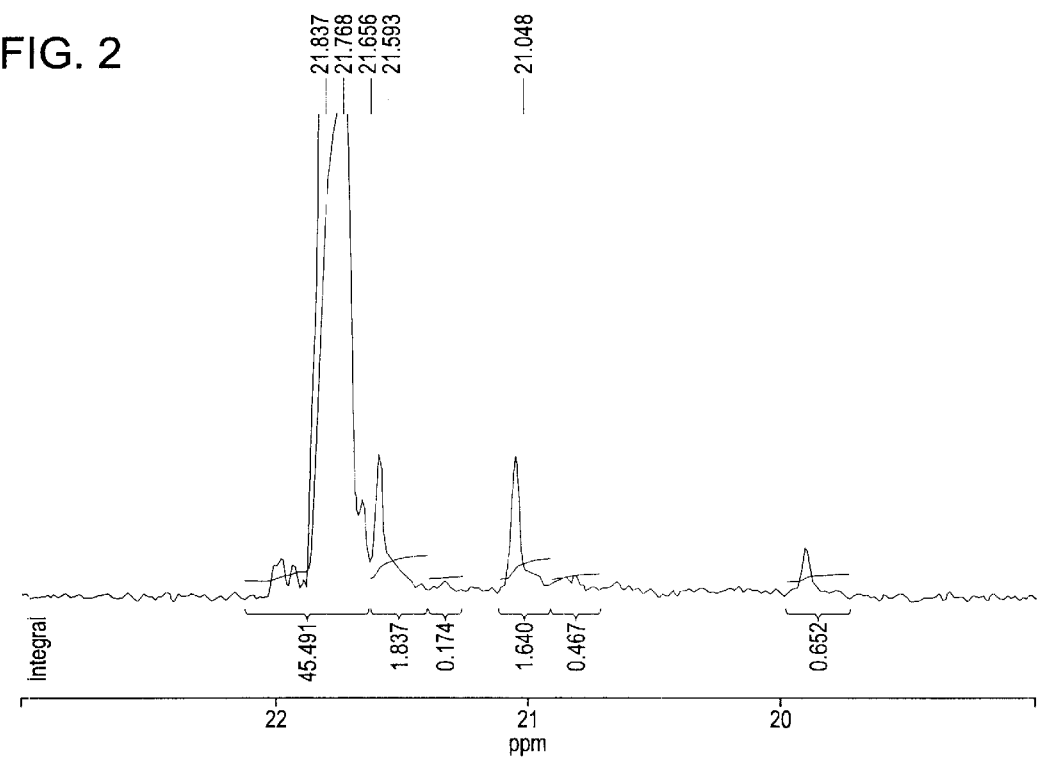
FIG. 2 shows a 13C NMR spectrum of polypropylene produced in accordance with the present invention.
Figure 3:
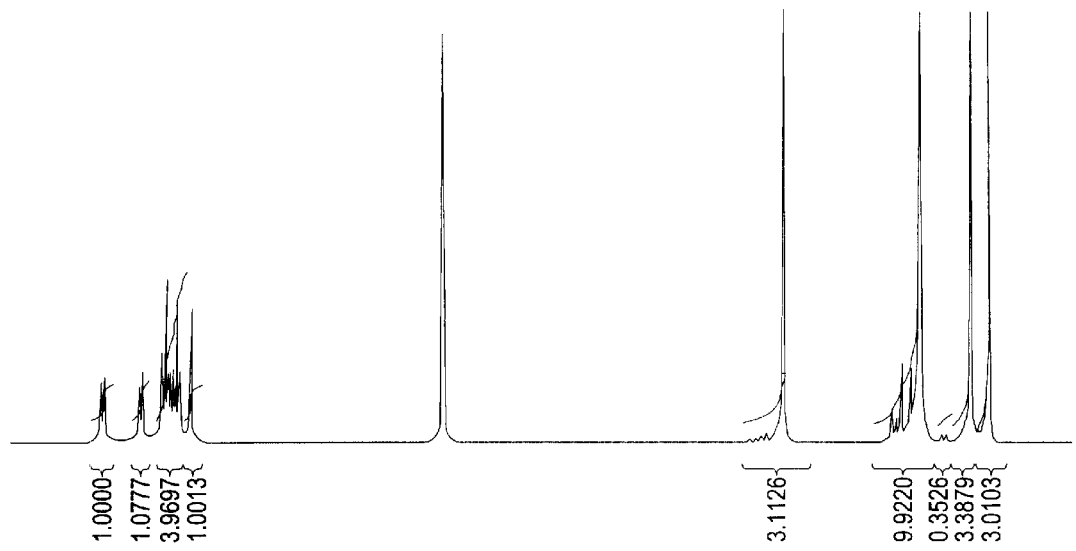
FIG. 3 shows the results of differential scanning calorimetry on the polypropylene.

FIG. 2 shows a 13C NMR spectrum of the polymer and FIG. 3 shows a HNMR spectrum of the metallocene in CO$_2$Cl$_2$ at 25° C.

TABLE 1

Polymerization with (Me$_2$Si($^t$buN) (2-MeBenzInd) ZrCl$_2$)$_2$

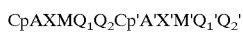

| Pol. Temp (° C.) | Residence time (mins) | Mn (Da) | Mw (Da) | Mz (Da) | D | D' | Melt. Temp (° C.) |
|---|---|---|---|---|---|---|---|
| 60 | 60 | 60,900 | 259,800 | 704,000 | 4.3 | 2.7 | 146.9 |

TABLE 2

Microtacticity with (Me$_2$Si ($^t$buN) (2-MeBenzInd) ZrCl$_2$)

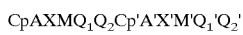

| PENTADS Sequence | % |
|---|---|

TABLE 2-continued

| Microtacticity with (Me$_2$Si ($^t$buN) (2-MeBenzInd) ZrCl$_2$) | |
|---|---|
| mmmm | 86.93 |
| mmmr | 4.94 |
| rmmr | 1.14 |
| mmrr | 3.66 |
| rmrr + mrmm | 0.64 |
| mrmr | 0.60 |
| rrrr | 0.39 |
| mrrr | 0.41 |
| mrrm | 1.29 |
| TRIADS Sequence | % |
| mm | 93.01 |
| mr | 4.90 |
| rr | 2.09 |
| DYADS Sequence | % |
| m | 95.46 |
| r | 4.54 |
| Misinsertions | mole % |
| 2,1 | 0.33 |
| 1,3 | 0.00 |

What is claimed is:

1. A process of making a metallocene catalyst component comprising contacting (a) a metallocene compound having the general formula:

CpAXMQ$_1$Q$_2$Cp'A'X'M'Q$_1$'Q$_2$' wherein Cp and Cp' are each independently a substituted or un substituted cyclopentadienyl moiety wherein each said cyclopentadienyl moiety is substituted or unsubstituted indenyl; M and M' are each a metal chosen from Group IV B transition metals and vanadium, and coordinate to Cp and Cp' respectively; X and X' are each independently a substituted or unsubstituted Group VA or VIA heteroatom and coordinate to M and M' respectively; A and A' are bridging groups between Cp and X and between Cp' and X' respectively and are independently chosen from —SiR'$_2$—O—SiR'$_2$—Si$_n$R$_m$—, —C$_n$R'$_m$— and —CR'$_2$—SiR'$_2$—CR'$_2$—SiR'$_2$—, in which each R' is independently H or hydrocarbyl having 1 to 20 carbon atoms, n is an integer in the range 1 to 4 and m–2n; each Q$_1$, Q$_2$ and Q$_1$' and Q$_2$' is independently a coordinating group which is hydrogen, halogen, or hydrocarbyl having 1 to 20 carbon atoms and each of Q$_1$ and Q$_1$' is coordinated to both M and M'; and (b) an aluminum- or boron-containing cocatalyst capable of activating the metallocene compound.

2. A process according to claim 1, wherein the metallocene compound is (t-butylamido) (2-methyl-4,5-benzoinden-1-yl)-1,1-dimethyl silane zirconium chloride or (t-butylamido) (2-methyl-4,5-benzoinden-1-yl)-1,1-dimethyl silane titanium chloride.

3. A catalyst system for use in preparing polyolefins, which comprises (a) a metallocene compound having the general formula:

CpAXMQ$_1$Q$_2$Cp'A'X'M'Q$_1$'Q$_2$' wherein Cp and Cp' are each independently a substituted or un substituted cyclopentadienyl moiety wherein each said cyclopentadienyl moiety is substituted or unsubstituted indenyl; M and M' are each a metal chosen from Group IV B transition metals and vanadium, and coordinate to Cp and Cp' respectively; X and X' are each independently a substituted or unsubstituted Group VA or VIA heteroatom and coordinate to M and M' respectively; A and A' are bridging groups between Cp and X and between Cp' and X' respectively and are independently chosen from —SiR'$_2$—O—SiR'$_2$—SiR$_1$—C$_n$R'$_m$ and —CR'$_2$—SiR'$_2$—CR'$_2$—SiR'$_2$—, in which each R' is independently H or hydrocarbyl having 1 to 20 carbon atoms, n is an integer in the range 1 to 4 and m–2n; each $Q_1$, $Q_2$ and $Q_1'$ and $Q_2'$ is independently a coordinating group which is hydrogen, halogen, or hydrocarbyl having 1 to 20 carbon atoms and each of $Q_1$ and $Q_1'$ is coordinated to both M and M'; and (b) an aluminum- or boron-containing cocatalyst capable of activating the metallocene compound.

4. A catalyst system according to claim 3, which further comprises an inert support.

5. The process of claim 1 wherein each indenyl moiety is substituted or unsubstituted benzoindenyl.

6. The process of claim 1 wherein said cyclopentadienyl moiety is substituted at position 2 with a hydrocarbyl having 1 to 20 carbon atoms.

7. The process of claim 1 wherein said metal is Zr.

8. The process of claim 1 wherein said heteroatom is nitrogen, phosphorous, oxygen or sulphur an di substituted with H, hydrocarbyl having 1 to 20 carbon atoms or silyl.

9. The process of claim 1 wherein said heteroatom is nitrogen.

10. The process of claim 1 wherein each A and A' is SiR'$_2$.

11. The process of claim 1 wherein each R' is methyl.

12. The process of claim 1 wherein said metallocene compound has an active site and wherein said active site has local C2 symmetry.

13. The process of claim 1 wherein said metallocene compound has a dimeric structure.

14. The catalyst system of claim 3 wherein each indenyl moiety is substituted or unsubstituted benzoindenyl.

15. The catalyst system of claim 3 wherein said cyclopentadienyl moiety is substituted at position 2 with a hydrocarbyl having 1 to 20 carbon atoms.

16. The catalyst system of claim 3 wherein said metal is Zr.

17. The catalyst system of claim 3 wherein said heteroatom is nitrogen, phosphorous, oxygen or sulphur an di substituted with H, hydrocarbyl having 1 to 20 carbon atoms or silyl.

18. The catalyst system of claim 3 wherein said heteroatom is nitrogen.

19. The catalyst system of claim 3 wherein each A and A' is SiR'$_2$.

20. The catalyst system of claim 3 wherein each R' is methyl.

21. The catalyst system of claim 3 wherein said metallocene compound has an active site and wherein said active site has local C2 symmetry.

22. The catalyst system of claim 3 wherein said metallocene compound has a dimeric structure.

23. The catalyst system of claim 3 wherein said metallocene compound is (t-butylamido) (2-methyl-4,5-benzoinden-1-yl)-1,1-dimethyl silane zirconium chloride or (t-butylamdio) (2-methyl-4,5-benzoinden-1-yl)-1,1-dimethyl silane titanium chloride.

* * * * *